(12) United States Patent
Cui

(10) Patent No.: US 7,785,581 B2
(45) Date of Patent: Aug. 31, 2010

(54) COMPOSITION AND METHOD FOR REDUCING FECES TOXINS AND TREATING DIGESTIVE DISORDERS

(75) Inventor: Yunlong Cui, Jiaonan (CN)

(73) Assignee: Qingdao East Sea Pharmaceuticals Ltd., Jiaonan (CN)

( * ) Notice: Subject to any disclaimer, the term of this patent is extended or adjusted under 35 U.S.C. 154(b) by 537 days.

(21) Appl. No.: 11/707,607

(22) Filed: Feb. 16, 2007

(65) Prior Publication Data

US 2008/0199444 A1 Aug. 21, 2008

(30) Foreign Application Priority Data

Jun. 26, 2006 (CN) ................ 2006 1 0086642
Nov. 17, 2006 (CN) ................ 2006 1 0138486

(51) Int. Cl.
*A61K 31/70* (2006.01)
*A61K 35/74* (2006.01)
*A61P 1/00* (2006.01)

(52) U.S. Cl. ............... 424/93.41; 424/93.4; 424/93.46; 514/23

(58) Field of Classification Search ............... None
See application file for complete search history.

(56) References Cited

U.S. PATENT DOCUMENTS 6,723,326 B1 4/2004 Farmer

2004/0028689 A1 2/2004 Borody
2005/0100535 A1 5/2005 Farmer et al.
2006/0127381 A1 6/2006 Cui

FOREIGN PATENT DOCUMENTS

| EP | 1 022 023 | 10/2005 |
|---|---|---|
| WO | WO00/61201 | 10/2000 |
| WO | WO01/34168 | 5/2001 |

OTHER PUBLICATIONS

Gregor Reid (Current Infectious Disease Reports. 2000; 2: 78-83).*
Wan et al., "Effect of *Bacillus coagulans* tablets on the treatment of experimental diarrhea in mice," Chinese J. Microecology 17(6):415-418 (2005).
Cui et al., "Inhibitory effect of *Bacillus coagulans* TBC 169 strain on the pathogenic bacteria in intestinal tract," Chinese J. Microecology 17(5):333-338 (2005).
Wang et al., "The effects of *Bacillus coagulans* on immune functions, amine content of feces and ammonia content of intestinal tract in mice," Chinese J. Microecology 18(1):6-8(2006).

* cited by examiner

*Primary Examiner*—Scott Long
(74) *Attorney, Agent, or Firm*—Occhiuti Rohlicek & Tsao LLP

(57) ABSTRACT

This invention relates to a method of lowering feces toxin levels and treating digestive disorders (e.g., Irritable Bowel Syndrome or diarrhea) with a composition containing a live beneficial bacterium, a prebiotic, or both. This method includes first identifying a subject in need thereof and then administering to the subject an effective amount of the composition. Also within the scope of this invention is a composition including both a live beneficial bacterium and a prebiotic.

13 Claims, No Drawings

COMPOSITION AND METHOD FOR REDUCING FECES TOXINS AND TREATING DIGESTIVE DISORDERS

CROSS-REFERENCE TO RELATED APPLICATIONS

This application claims the benefit of Chinese Patent Application No. 200610086642.3, filed Jun. 26, 2006, and Chinese Patent Application No. 200610138486.0, filed Nov. 17, 2006. The contents of both of these applications are incorporated herein by reference in their entireties.

BACKGROUND

The repellent smell of feces comes from compounds (feces toxins) such as amine, ammonia, hydrogen sulfide, 3-methyl indole, indole, phenol, and thiol. Excess feces toxins are known to cause various medical, in particular, digestive, conditions and diseases, in particular, digestive conditions and disorders. They can act directly on intestinal and colonic walls, resulting in local inflammation or tissue damage. The toxins also can penetrate through these walls to enter the blood stream, thus circulating around the whole body and damaging other organs.

Irritable Bowel Syndrome (IBS) is one of the digestive disorders that may be associated with feces toxins. An IBS patient typically has abdominal discomfort, abdominal pain, constipation, diarrhea, or bloating. While several means may help alleviate the symptoms (e.g., exercise or intake of high fiber diet), currently there is no cure for IBS, Diarrhea is a medical condition caused by various diseases (e.g., intestinal infection, intestinal inflammation, malabsorption, or anxiety), some of which may be attributable to feces toxins. A diarrhea patient suffers frequent bowel evacuation or passage of abnormally soft or liquid feces. Treatment of diarrhea depends on its causes. Traditional means to alleviate diarrhea include combined administration of liquid, nutrients, and medication.

SUMMARY

The present invention is based on the unexpected discoveries that live bacteria, such as *Bacillus, Clostridium*, and *Bifidobacterium*, reduce the feces toxin levels, and that these bacteria are effective in treating IBS and diarrhea.

In one aspect, this invention features a method of reducing the levels of feces toxins by first identifying a subject in need thereof and then administering to the subject an effective amount of a composition containing a live beneficial bacterium, a prebiotic, or both. This composition can be a pharmaceutical product, a food product, or a food supplement.

One or more (e.g., 1-5) live beneficial bacteria, such as *Bacillus, Clostridium*, or *Bifidobacterium*, can be included in this composition. For example, the composition can contain three different types of bacteria *Bacillus, Clostridium*, and *Bifidobacterium*. The *Bacillus* can be *Bacillus subtillis*, or *Bacillus coagulans*. The *Clostridium* can be *Clostridium butyricum*. The *Bifidobacterium* can be *Bifidobacterium adolescentis, Bifidobacterium longum, Bifidobacterium bifidum, Bifidobacterium breve*, or *Bifidobacterium infantis*. Certain strains of *Bacillus coagulans, Clostridium butyricum, Bifidobacterium longum, Bifidobacterium bifidum, Bifidobacterium breve*, and *Bifidobacterium infantis* were deposited at the Chinese General Microbiological Culture Collection Center (CGMCC), Institute of Microbiology, Chinese Academy of Sciences, Haidian, Beijing 100080, P.O.Box 2714 under the Budapest Treaty and have been assigned deposit numbers CGMCC No. 1207, CGMCC No. 0313.1, CGMCC No. 0313.5, CGMCC No. 0313.7, CGMCC No. 0313.6, and CGMCC No. 0313.2, respectively. CGMCC No. 1207 was deposited on Aug. 23, 2004 and CGMCC No. 0313.1, CGMCC No. 0313.5, CGMCC No. 0313.7, CGMCC No. 0313.6, and CGMCC No. 0313.2 were deposited on Jul. 28, 1997. The effective amount of these beneficial live bacteria is within the range of $10^6$-$10^{12}$ cfu per day.

Similarly, one or more prebiotics, e.g., oligosaccharides, can be included in this composition. The oligosaccharide can be fruto-oligosaccharide G, isomalto-oligosaccharide, inulin, lactilol, lactosucrose, lactulose, pyrodextrin, soy oligosaccharide, galacto-oligosaccharide, xylo-oligosaccharide, isomalto-oligosaccharide,stachyose, raffinose or trehalose. The effective amount of a prebiotic can be within the range of 0.7 g to 30 g per day. In particular, the effective amount of soy oligosaccharide or galacto-oligosccharide is at least 10 g per day; that of fructo-oligosaccharide G is at least 3 g per day; and that of xylo-oligosaccharide is at least 0.7 g per day.

In another aspect, this invention features a method of treating a subject suffering from IBS by first identifying such a subject and then administering to that subject an effective amount of the above-described composition.

This composition can also be used to treat (1) a subject who suffers from diarrhea caused by eating cold or raw food, or drinking alcohol within 24 hours, and (2) a subject who suffers from both diarrhea and common cold.

Also within the scope of this invention is a composition containing a live beneficial bacterium and a prebiotic, as well as the use of the composition for the manufacture of a medicament for reducing feces toxin levels and for treating IBS and diarrhea.

Details about the live bacterium and the prebiotic are described above.

The details of one or more embodiments of the invention are set forth in the description below. Other features, objects, and advantages of the invention will be apparent from the description and from the claims.

DETAILED DESCRIPTION

The present invention features a method of lowering the feces toxin levels in a subject in need thereof with a composition containing a live beneficial bacterium, a prebiotic, or a combination thereof.

The levels of the repellent smell of feces are determined by the following standard: 0: no smell; 1-3: unpleasant; 4-6: repellent; 7-10: highly repellent. Generally, the feces smell of a patient who needs this treatment has a level of 3 or above. In most cases, such feces display abnormal physical features, e.g., loose, watery, or lumpy. The subject usually also has digestive conditions and disorders, e.g., constipation, diarrhea, and IBS.

Beneficial bacteria in the intestine and colon benefit their host in various ways. For example, they can form on the top of the intestinal and colonic walls a protective layer, which blocks harmful bacteria and their toxins from damaging or penetrating the walls. In addition, most beneficial bacteria secret acidic substances (e.g., short-chain fatty acids) resulting in an acidic environment unsuitable for the growth of harmful bacteria. Moreover, beneficial bacteria generate digestive enzymes to decompose food. They also promote digestion by secreting the just-mentioned short-chain fatty acids, which stimulate intestine and colon movement.

The term "beneficial bacterium" refers to any bacterium that has one or more of the features described above.

The live beneficial bacteria can be prepared by fermentation carried out under various conditions. A bacterium can be cultured individually or co-cultured with another bacterium. After the fermentation, the bacteria can be collected by centrifugation and the resultant wet pellets are then dried by a method that preserves the activity of the bacteria. Suitable drying methods include freeze drying, spray drying, heat drying, or a combination thereof.

The bacteria powder thus obtained can be mixed with a pharmaceutically acceptable carrier. Suitable carriers include microcrystalline cellulose, mannitol, glucose, defatted milk powder, polyvinylpyrrolidone, and starch, or a combination thereof. The mixture of the bacteria powder and the carrier can then be presented in a variety of forms, such as tablet, capsule, or liquid.

The bacteria powder also can be part of a food product (e.g., yogurt, milk, or soy milk) or a food supplement (e.g., supply nutrients or herbal products). Such food products and food supplements can be prepared by methods well known in the food industry.

Effective amounts of the live bacterium used in this method can be determined based on factors such as feces toxins levels, duration of excreting feces of a highly repellent smell, age, and health condition. In general, the effective amount ranges from $10^6$ to $10^{12}$ cfu per day.

The live bacterium can be administered to a subject via suitable routes, e.g., oral administration or rectal administration. It can be administered once or multiple times per day or administered once every several days. The treatment can last from several days to several weeks, depending on the needs.

Other than live bacteria, one or more prebiotics can be used instead to lower feces toxin levels in a subject. Prebiotics can selectively stimulate the growth or activity of a number of beneficial bacteria in the intestine or colon, thus indirectly inhibiting the growth of harmful bacteria. Most prebiotics are non-digestible oligosaccharides, e.g., fruto-oligosaccharide Q isomalto-oligosaccharide, soy oligosaccharide, galacto-oligosaccharide, or xylo-oligosaccharide. They can be isolated from natural sources or prepared by synthetic methods. Their effective amounts, generally ranging from 0.7 g to 30 g per day, can be determined based on the factors discussed above. They can be formulated and administered in the same manners as live bacteria.

If necessary, one can use a composition containing both a live beneficial bacteria and a prebiotics to reduce the feces toxin levels in a subject in need thereof. In this embodiment, the effective amounts of the live bacterium and the prebiotic should be at least their lowest effective amounts when used individually, i.e., $10^6$ cfu per day for a live bacterium and 0.7 g for a prebiotic. The bacteria and the prebiotics can be formulated separately or together. In the former situation, they can be administered simultaneously or sequentially.

The composition described above can also be used to treat IBS and diarrhea, which is caused by eating cold/frozen or raw food or drinking alcohol within 24 hours, or is associated with common cold.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Preparation of Bacteria Powder Containing Live *Clostriduim Butyricum*

*Clostriduim butyricum* CGMCC No. 0313.1 stored in a tube was suspended in a 100 ml autoclaved Erlenmeyer flask containing 10 ml physiological saline and suitable amount of glass beads. After 10 minutes, 1 ml bacteria solution was inoculated into a 250 ml Erlenmeyer flask filled with 50 ml amplification media containing tryptone (1%), yeast extract (0.3%), beef exact (1%), glucose (0.5%), soluble starch (0.1%), sodium chloride (0.5%), anhydrous sodium acetate (0.3%), and L-cysteine (0.05%). The bacteria were cultured in a shaker at 37° C. and shaken at the speed of 190 rpm for 24 hours. Then the bacteria solution was transferred to a 2500 ml baffled Erlenmeyer flask containing 450 ml amplification media, cultured at 37° C. with shaking for another 24 hours. The bacteria solution was examined under microscope for contamination. If no contamination had occurred, the bacteria solution was transferred into a seeding tank containing 4.5 L amplification media and further cultured under aerobic conditions (air inflation amount 3:1) for yet another 24 hours. The resulting bacteria solution, if not contaminated, was transferred to a fermentation tank filled with fermentation media and cultured under aerobic conditions for 24 hours. When the sporulation rate reached 80% (determined by microscopic examination), the fermentation was terminated. The bacteria were collected by centrifuging at 12,000 rpm. Wet bacteria pellets were collected and weighed. The same amount (by weight) of defatted milk powder was mixed with the bacteria, dried, pulverized and kept at room temperature ready for use.

EXAMPLE 2

Effects of Live *B. Coagulans* and *C. Butyricum* on the Levels of Amine and Ammonia in Mouse Feces and Intestines Fifty ICR mice were randomly divided into five groups, 10 in each group. Mice in each group were orally administered with $10^9$ cfu *B. coagulans* CGMCC No. 1207, $10^8$ cfu *B. coagulans* CGMCC No. 1207, $10^9$ cfu *C. butyricum* CGMCC0313.1, $10^8$ *C. butyricum* CGMCC0313.1, or physiological saline, in a total volume of 0.5 ml/per mouse, once per day for 21 days. At day 20, mice in each group were kept separately in individual cages and feces from each cage were collected. Same amount (by weight) of feces from each cage was suspended in saline, centrifuged, and then supernants were collected. The amount of amine (μg/g) in each supernant sample was determined, using the neutralization method described in WANG et al., *Chinese Journal of Microecology*, 2006,18(1):6-8)

The treated mice were sacrificed at day 21, their appendix excised and weighed. Same amount of the appendix from each mouse was then grounded and suspended in physiological saline. After centrifugation, the supernants were collected and the amount of ammonia contained therein was quantified (μg/g) following the method described in YIN et al., *Chinese Journal of Microecology*, 2003, 15(4):212.

Both *B. coagulans* CMGCC No. 1207 and *C. butyricum* CGMCC0313.1 reduced the quantities of amine and ammonia in mouse feces and intestines at both dosages, respectively. Statistical analysis using Analysis of Variance (ANOVA) showed that the reductions were significant ($P<0.05$), compared to control mice (treated with saline).

EXAMPLE 3

Effects of *B. Coagulans* and *C. Butyricum* on the Levels of Indole and 3-methyl-indole in Human Feces Sixteen volunteers (six male and ten female, age 25-55) were randomly divided into two groups, one taking tablets containing live *B. coagulans* CMGCC No. 1207 and the other capsules containing live *C. butyricum* CMGCC No. 0313.1. The amount of the live bacterium contained in each tablet is $1.75\times10^7$ cfu and in each capsule is $0.42\times10^7$ cfu. Each volunteer took three *B. coagulans* tablets or three *C. butyricum* capsules after each meal, three times per day, for 14 days. During this period, all volunteers maintained their regular diets. Feces were collected before and after taking the tablets or capsules and the levels of indole and 3-methyl-indole contained therein were quantified using HP-6890 HPLC.

Half gram (0.5 g) fresh feces were suspended in 20 ml ethanol and extracted by ultrasound for 20 minutes. The solutions were then filtered, added with 3 ml 0.1% p-Isopropylphenol as an internal control, and diluted to 25 ml in a 25-ml volumetric flask. Four microliters (4 µl) of the above solution were injected into a chromatography column (HP-INNO WAX glass capillary, 30 m×0.53 mm, filled with 17% silicone SE-30) and analyzed under the following conditions: column temperature: 200° C.; sample injection system temperature: 230° C.; detector temperature: 260° C., $N_2$ flow rate: 90 ml/min; $H_2$ flow rate: 58 ml/min; air flow rate: 60 ml/min.

Both the *B. coagulans* tablets and the *C. butyricum* capsules significantly reduced the levels of indole and 3-methyl-indole contained in the volunteers' feces. Statistical analysis showed that these reductions are significant.

EXAMPLE 4

Effects of *B. coagulans* on Physical Features of Human Feces and Symptoms of Digestive Disorders Forty-two volunteers (20 male and 22 female, age 20-30) were taken tablets containing live *B. coagulans* CMGCC No. 1207 (at least $0.35\times10^7$ cfu per tablet), 3 tablets after each meal, three times per day, for seven days. All volunteers had maintained their regular diets in this period. Physical features of their feces, such as odor, shape, and color, were observed immediately after every bowel movement. The normal and abnormal physical features of feces are summarized in Table 1.

Feces of all 42 volunteers displayed one or more abnormal physical features before taking the *B. coagulans* tablets. Some volunteers also showed symptoms of digestive disorders, such as constipation, loss of appetite, bellyache, and borborygmus. After treatment, most volunteers showed significantly reduced abnormal features of their feces. These volunteers also had alleviated symptoms of digestive disorders.

TABLE 1

Physical features of normal and abnormal feces:

| | Normal | Abnormal |
|---|---|---|
| Color | yellow, yellowish brown or yellowish green | dark brown, black or grey |
| Shape/hardness | soft or slightly solid, banana-shaped | hard, lumpy, loose or watery |
| Repellent smell* | Levels 0-2 | Levels 3 and above |

*See standard described above.

EXAMPLE 5

Joint Effects of *B. Coagulans* and Xylo-oligosaccharides on the Physical Features of Human Feces Sixty volunteers (30 male and 30 female, age 20-50), who had maintained their regular diets, were taken 3 tablets containing both live *B. coagulans* CMGCC No. 1207 and xylo-oligosaccharide, after each meal, three times per day, for seven days. Each tablet contains at least $0.35\times10^7$ cfu live bacteria and at least 0.10 g xylo-oligosaccharide. During this period, physical features of their feces as described above were observed immediately after every bowel movement.

Feces of all 60 volunteers displayed one or more abnormal physical features before taking the tablets. Some of the volunteers also showed symptoms of digestive disorders, such as constipation, loss of appetite, bellyache, and borborygmus. After treatment, most volunteers showed significantly reduced abnormal features of their feces. Their symptoms of digestive tract disorders were also alleviated.

EXAMPLE 6

Effects of Live *C. Butyricum* in Treating Irritable Bowel Syndrome (IBS)

Fifty IBS patients, diagnosed according to the Roman II standards described in Table 2, were treated with capsules containing *C. butyricum* CGMCC No. 0313.1, three capsules each time, twice a day, for 14 to 21 days. Each capsule contains at least $1.0\times10^6$ cfu/g live bacteria. During this period, these patients were observed for IBS symptoms, e.g., abdominal pain, constipation, or diarrhea.

TABLE 2

Roman II Standards:

| Degree of Pain | | Degree of Bloating | | Degree of Stool Passage - Straining, incomplete, or Urgent | | Degree of Borborygmus | | Pain while pressing abdomen | |
|---|---|---|---|---|---|---|---|---|---|
| No Pain | 0 | No | 0 | No | 0 | Normal | 0 | No | 0 |
| Slight, does not affect daily | 1 | Rare | 1 | Rare | 1 | active | 1 | Slight | 1 |

TABLE 2-continued

| | Roman II Standards: | | | | | | | | |
|---|---|---|---|---|---|---|---|---|---|
| Degree of Pain | | Degree of Bloating | | Degree of Stool Passage - Straining, incomplete, or Urgent | | Degree of Borborygmus | | Pain while pressing abdomen | |
| activity Intermediate pain, affect daily activities, need medication | | 2 Occasional | | 2 Occasional | | 2 slightly hyperactive | | 2 Pain | 2 |
| Severe pain, affect daily activities, need medication and rest | | 3 Frequent | | 3 Frequent | | 3 Hyperactive | | 3 Severe pain | 3 |

Standards of efficacy are described below:
Cured: Patients' feces display normal physical features. Patients have normal numbers of bowel movement every day, i.e., 1-2 times, with yellow, shaped feces. No other IBS symptoms.
Effective: Patients have obviously improved physical features of their feces and obviously alleviated IBS symptoms, e.g., 2-3 times bowel movement per day or >3 times per week, with yellow, soft feces.
Improved: Patients have improved physical features of their feces and alleviated IBS symptoms, e.g., 3 times bowel movement per day, or 3 times per week, with yellow, loose feces.
Ineffective: Patients have no improvement as to physical features of their feces and other IBS symptoms.

All of the IBS patients showed one or more IBS symptoms before treatment. After taking the *C. butyricum* capsules for averagely two days, symptoms of diarrhea or constipation started ameliorating. Other IBS symptoms, such as abdominal pain and discomfort were also alleviated in these patients. The rate of complete recovery (cured) was 62% (31/50) and the overall effective rate was 94% (47/50), see Table 3. No side effects were observed during this treatment.

TABLE 3

Efficacy of treating IBS with live *C. butyricum*

| Cured | | Effective | | Improved | | Ineffective | | Effective Cases | |
|---|---|---|---|---|---|---|---|---|---|
| Case No. | Case No. % | Case No. | % | Case No. | % | Case No. | % | Case No. | % |
| 50 | 31 62 | 16 | 32 | 3 | 6 | 0 | 0 | 47 | 94 |

EXAMPLE 7

Effects of Live *B. Coagulans* in Treating IBS

Forty-six IBS patients (male 29, female 17, average age 43.5±11.9) were participated in this study. These patients had IBS symptoms for 22.9 months in average. Among them, 30 patients had diarrhea, 6 constipation, and 10 both diarrhea and constipation. They were orally administered with tablets containing live *B. Coagulans* CGMCC No. 1207, three tablets each time, three times a day, for 14 to 21 days. Each tablet contains at least $1.0 \times 10^6$ cfu/g live bacteria. During this period, these patients were observed for IBS symptoms, e.g., abdominal pain, constipation, or diarrhea. The efficacy of this treatment was determined according to the above-described standards.

All of the IBS patients showed one or more IBS symptoms before treatment. After taking the *B. Coagulans* tablets, most of these patients had ameliorated symptoms of diarrhea or constipation. Other IBS symptoms, such as abdominal pain and discomfort were also alleviated in these patients. The efficacy of treating IBS with *B. Coagulans* tablets are shown in Table 4. The rate of complete recovery (cured) was 65% (30/65) and the overall effective rate was 93% (43/46). No side effects were observed during this treatment.

TABLE 4

Efficacy of treating IBS with *B. Coagulans* Tablets

| Cured | | Effective | | Improved | | Ineffective | | Effective Cases | |
|---|---|---|---|---|---|---|---|---|---|
| Case No. | Case No. % | Case No. | % | Case No. | % | Case No. | % | Case No. | % |
| 46 | 30 65 | 13 | 28 | 3 | 7 | 0 | 0 | 43 | 93 |

EXAMPLE 8

Effects of Live *Bifidobacterium* on IBS

Fifty-seven IBS patients (male 35, female 22, average age 40.5±10.8) were participated in this study. These patients had IBS symptoms for 20.5 months in average. Among them, 38 patients had diarrhea, 9 constipation, and 10 both. They were orally administered with tablets containing live *Bifidobacterium infantis* CGMCC No.0313.2, three tablets each time, three times a day, for 14 to 21 days. Each tablet contains at least $1.0 \times 10^6$ cfu/g live bacteria. During this period, patients were observed for IBS symptoms, e.g., abdominal pain, constipation, or diarrhea. The efficacy standards are the same as described above.

After taking the *Bifidobacterium* tablets, most of these patients had ameliorated symptoms of diarrhea or constipation. Other IBS symptoms, such as abdominal pain and discomfort, were also alleviated in these patients. The efficacy of treating IBS with the *Bifidobacterium* tablets are shown in Table 5. The rate of complete recovery (cured) was 61% (35/57) and the overall effective rate was 89% (51/57). No side effects were observed during this treatment.

TABLE 5

Efficacy of treating IBS with live *Bifidobacterium*

| Cured | | Effective | | Improved | | Ineffective | | Effective Cases | |
|---|---|---|---|---|---|---|---|---|---|
| Case No. | Case No. | % | Case No. | % | Case No. | % | Case No. | % | Case No. | % |
| 57 | 35 | 61 | 16 | 28 | 6 | 11 | 0 | 0 | 51 | 89 |

EXAMPLE 9

Effects of Live *Bacillus, Clostridium*, and *Bifodobacterium* in Treating Diarrhea Associated with Cold or Raw Food, or with Common Cold One hundred and twenty-seven patients (male 79, female 48, age 18-70, average age 39) were selected for this study. All of them showed one of the following symptoms within 24 hours after eating cold/raw food, or developing a common cold: (1) abdominal pain or discomfort coupled with frequent bowel movement (>3 times per 24 hours), (2) abdominal pain or discomfort coupled with changes in physical features of feces (loose, watery etc.), and (3) diarrhea that has been lasted for 2 weeks to 2 months.

These patients were orally administered with capsules containing live *C. butyricum* CGMCCNo.0313.1 (420 mg per capsule), tablets containing live *B. coagulans* CGMC-CNo.1207 (350 mg per tablet), or *Bifidobacterium infantis* CGMCCNo.0313.2 (350 mg per tablet), three capsules/tablets each time, three times per day, for 14 to 21 days. In each capsule or tablet, the amount of live bacteria is at least $1.0 \times 10^6$ cfu/g. Symptoms such as frequency of bowel movement, physical features of feces, abdominal pain and discomfort, bloating, or borborygmus, were observed immediately after termination of the treatment. The standards to determine efficacy are the same as described above.

Live bacteria of *C. butyricum, B. coagulans*, and *Bifidobacterium* are highly effective in treating diarrhea associated with eating cold or raw foods, or with common cold. These patients had significantly reduced numbers of bowel movement per day after taking the tablets or capsules. In addition, most of the patients had improved physical features of their feces and reduced abnormal bowel movement after taking these drugs. Other symptoms, such as abdominal pain, bloating, and borborygmus, were also alleviated in these patients. The overall efficacy of this treatment is summarized in Table 6.

TABLE 6

Efficacy of live *C. butyricum, B. coagulans*, and *Bifidobacterium* on diarrhea

| Bacterium Used | Case No. | Cured | Effective | Improved | Ineffective | Efficacy |
|---|---|---|---|---|---|---|
| C. butyricum | 45 | 26 | 15 | 4 | 0 | 91.10% |
| B. coagulans | 40 | 25 | 12 | 3 | 0 | 92.50% |
| Bifidobacterium | 42 | 23 | 14 | 5 | 0 | 88.10% |

EXAMPLE 10

Effects of *Bacillus, Clostridium*, and *Bifidobacterium* in Treating Diarrhea Associated with Alcohol Intake One hundred and fourteen patients (male 100, female 14, age 18-70, average age 40) were selected for this study. All of them showed one of the following symptoms within 24 hours after drinking alcohol: (1) abdominal pain or discomfort coupled with frequent bowel movement (>3 times per 24 hours), (2) abdominal pain or discomfort coupled with changes in physical features of feces (loose, watery etc.), and (3) diarrhea that has been lasted for 2 weeks to 2 months.

These patients were orally administered with capsules containing live *C. butyricum* CGMCCNo.0313.1 (420 mg per capsule), tablets containing live *B. coagulans* CGMC-CNo.1207 (350 mg per tablet), or *Bifidobacterium infantis* CGMCCNo.0313.2 (350 mg per tablet), three capsules/tablets each time, three times per day, for 14 to 21 days. In each capsule or tablet, the amount of the live bacterium is at least $1.0 \times 10^6$ cfu/g. Symptoms such as frequency of bowel movement, physical features of feces, abdominal pain and discomfort, bloating, or borborygmus were observed immediately after termination of the treatment. The standards to determine efficacy is the same as described above.

Live bacteria of *C. butyricum, B. coagulans*, and *Bifidobacterium* are highly effective in treating diarrhea associated with alcohol intake. Patients treated with these live bacteria had significantly reduced numbers of bowel movement per day after the treatment. In addition, most of the patients had improved physical features of their feces and reduced abnormal bowel movement. Other symptoms, such as abdominal pain, bloating, and borborygmus, were also alleviated in these patients. The overall efficacy of this treatment is summarized in Table 7.

TABLE 7

Efficacy of live *C. butyricum, B. coagulans*, and *Bifidobacterium* on diarrhea associated with common cold

| Bacterium Used | Case No. | Cured | Effective | Improved | Ineffective | Efficacy |
|---|---|---|---|---|---|---|
| C. butyricum | 35 | 20 | 11 | 4 | 0 | 88.6% |
| B. coagulans | 41 | 27 | 9 | 5 | 0 | 87.8% |
| Bifidobacterium | 38 | 21 | 13 | 4 | 0 | 89.5% |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A composition comprising a prebiotic and a beneficial bacterium that is *Clostridium butyricum* CGMCC0313.1, *Bacillus coagulans* CGMCC No. 1207, *Bifidobacterium lon-*

*gum* CGMCC No. 0313.5, *Bifidobacterium bifidum* CGMCC No. 0313.7, *Bifidobacterium breve* CGMCC No. 0313.6, or *Bifidobacterium infantis* CGMCC No. 0313.2.

2. The composition of claim 1, wherein the beneficial bacterium is *Bacillus coagulans* CGMCC No. 1207.

3. The composition of claim 1, wherein the beneficial bacterium is *Bifidobacterium longum* CGMCC No. 0313.5, *Bifidobacterium bifidum* CGMCC No. 0313.7, *Bifidobacterium infantis*CGMCC No. 0313.2, or *Bifidobacterium breve* CGMCC No. 0313.6.

4. The composition of claim 1, wherein the composition comprises 1-5 live beneficial bacteria.

5. The composition of claim 1, wherein the prebiotic is oligosaccharide.

6. The composition of claim 4, wherein the oligosaccharide is fructo-oligosaccharide, isomalto-oligosaccharide, inulin, lactilol, lactosucrose, lactulose, pyrodextrin, soy oligosaccharide, galacto-oligosaccharide, or xylo-oligosaccharide.

7. The composition of claim 1, wherein the composition comprises more than one prebiotic.

8. The composition of claim 1, wherein the composition is a pharmaceutical product, a food product, or a food supplement.

9. The composition of claim 8, wherein the composition further is a pharmaceutical product.

10. A composition comprising a live beneficial bacterium selected from the group consisting of *Clostridium butyricum* CGMCC No. 0313.1, *Bacillus coagulans* CGMCC No. 1207, *Bifidobacterium longum* CGMCC No. 0313.5, *Bifidobacterium bifidum* CGMCC No. 0313.7, *Bifidobacterium infantis* CGMCC No. 0313.2, and *Bifidobacterium breve* CGMCC No. 0313.6, wherein the composition is a pharmaceutical composition, a food product, or a food supplement.

11. The composition of claim 10, wherein the composition is a pharmaceutical composition that further contains a pharmaceutically acceptable carrier.

12. The composition of claim 10, wherein the composition is a food product or a food supplement.

13. The composition of claim 11, wherein the beneficial bacterium is *Clostridium butyricum* CGMCC0313.1.

* * * * *